(12) United States Patent
Jiang et al.

(10) Patent No.: US 8,106,198 B2
(45) Date of Patent: Jan. 31, 2012

(54) PHOTOSENSITIZER DYE

(75) Inventors: Ke-Jian Jiang, Beijing (CN); Shuji Noda, Matsue (JP); Shozo Yanagida, Suita (JP)

(73) Assignee: Shimane Prefectural Government, Matsue (JP)

( * ) Notice: Subject to any disclaimer, the term of this patent is extended or adjusted under 35 U.S.C. 154(b) by 725 days.

(21) Appl. No.: 12/223,601

(22) PCT Filed: Feb. 5, 2007

(86) PCT No.: PCT/JP2007/051939
§ 371 (c)(1),
(2), (4) Date: Nov. 25, 2008

(87) PCT Pub. No.: WO2007/091525
PCT Pub. Date: Aug. 16, 2007

(65) Prior Publication Data
US 2009/0216021 A1    Aug. 27, 2009

(30) Foreign Application Priority Data
Feb. 8, 2006   (JP) ................................. 2006-031320

(51) Int. Cl.
C07F 15/00   (2006.01)
H01L 31/00   (2006.01)
(52) U.S. Cl. ............................. 546/2; 136/263; 556/137
(58) Field of Classification Search ...... 546/2; 556/137; 136/263
See application file for complete search history.

(56) References Cited

U.S. PATENT DOCUMENTS
| | | | |
|---|---|---|---|
| 6,639,073 B2 | 10/2003 | Islam et al. | |
| 2005/0081911 A1 | 4/2005 | Islam et al. | |

FOREIGN PATENT DOCUMENTS
| | | |
|---|---|---|
| EP | 1 622 178 A1 | 2/2006 |
| JP | A-2001-291534 | 10/2001 |
| JP | A-2003-212851 | 7/2003 |
| JP | A-2003-272721 | 9/2003 |
| JP | A-2004-296170 | 10/2004 |
| JP | A-2005-47857 | 2/2005 |
| JP | A-2005-120042 | 5/2005 |
| WO | WO 2006/010290 A1 | 2/2006 |
| WO | WO 2007/072970 A1 | 6/2007 |

OTHER PUBLICATIONS

Wang et al., "Enhance the Performance of Dye-Sensitized Solar Cells by Co-grafting Amphiphilic Sensitizer and Hexadecylmalonic Acid on $TiO_2$ Nanocrystals," J. Phys. Chem. B, vol. 107, No. 51, pp. 14336-14341, 2003.
Wang et al., "A stable quasi-solid-state dye-sensitized solar cell with an amphiphilic ruthenium sensitizer and polymer gel electrolyte," Nature Materials, vol. 2, pp. 402-407, Jun. 2003.
O'Regan et al., "A low-cost, high-efficiency solar cell based on dye-sensitized colloidal $TiO_2$ films," Letters to Nature, vol. 353, pp. 737-740, Oct. 24, 1991.
Wang et al., "A High Molar Extinction Coefficient Sensitizer for Stable Dye-Sensitized Solar Cells," J. Am. Chem. Soc., vol. 127, No. 3, pp. 808-809, 2005.
International Preliminary Report on Patentability mailed Oct. 8, 2009.
Supplementary European Search Report for European Patent Application No. 07708057.0 completed on Sep. 23, 2009.
Mohammad K. Nazeeruddin et al.; "Combined Experimental and DFT-TDDFT Computational Study of Photoelectrochemical Cell Ruthenium Sensitizers;" J. Am. Chem. Soc. 127(48); pp. 16835-16847; Nov. 12, 2005 (web).

*Primary Examiner* — Charanjit Aulakh
(74) *Attorney, Agent, or Firm* — Oliff & Berridge, PLC (57) ABSTRACT

A theme of the present invention is to provide a new transition metal complex, useful as a photosensitizer dye for a photoelectric conversion element having an excellent durability and a high photoelectric conversion characteristic. The present invention provides a bivalent transition metal complex constituted of (i) a bipyridyl polyacidic ligand, such as a dicarboxybipyridyl (dcbpy) ligand, as an adsorption site for adsorption onto titanium dioxide particle surfaces; (ii) a ligand, selected from the group consisting of an isothiocyanato group, an isocyanato group, and an isoselenocyanato group and enabling absorption and excitation at long wavelengths and charge transfer; and (iii) a bipyridyl (bpy) ligand, having an alkyl group or an alkoxy group, preferably a long-chain alkyl group, and a conjugately bonded thienylvinylene group, aminophenylenevinylene group, etc., and improving an absorbance of a transition metal complex and imparting stability against nucleophile to a sensitizer dye that improves an absorption bathochromic effect.

7 Claims, 7 Drawing Sheets

PHOTOSENSITIZER DYE

TECHNICAL FIELD

The present invention relates to a transition metal complex as a new photosensitizer dye that exhibits strong absorption over a wide spectral range and is excellent in stability, and to an oxide semiconductor electrode and a dye-sensitized solar cell containing the photosensitizer dye.

BACKGROUND ART

With fossil fuels becoming depleted and global warming occurring due to combustion thereof, development of new energies that can take the place of fossil fuels is becoming an urgent issue. Solar energy is a clean, environment-friendly energy source having adequate potential to support sustained development of future generations. As a method for converting solar energy to electricity, silicon-based semiconductor solar cells are being developed. However, the silicon used in such solar cells is required to be extremely high in purity and because a vast amount of energy is spent in a refining process and the process is complex, a high production cost is required.

Due to having comparatively high conversion efficiencies and being low in cost in comparison to conventional solar cells, dye-sensitized solar cells are becoming noted both in academia and business. In particular, with a dye-sensitized solar cell reported in 1991 by Graetzel et. al., a photoelectric conversion efficiency of 10 to 11% is achieved. With the dye-sensitized solar cell, a dye is adsorbed onto nanotitania particle surfaces to enable absorption of light in the visible range, and the role of the dye is particularly important due to exhibiting a light capturing action. As such dyes, cis-bis (isothiocyanato)-bis(2,2'-bipyridine-4,4'-carboxylate) ruthenium (II), which is denoted as N3, cis-bis(isothiocyanato)-bis (2,2'-bipyridine-4,4'-carboxylate) ruthenium (II) bis(tetra-n-butylammonium), which is denoted as N719, and cis-bis (isothiocyanato)-(2,2'-bipyridine-4,4'-carboxylate)-(2,2'-bipyridine-4,4'-dinonyl) ruthenium (II), which is denoted as Z907, have been developed until now. Although the dyes N3 and N719 exhibit high photoelectric conversion efficiencies, these have a problem in durability at a comparatively high temperature. This is due to the dye molecules desorbing from the titanium dioxide particle surfaces induced by the attack of water molecules, etc. On the other hand, Z907 is a type of amphiphilic ruthenium dye and is a dye of excellent stability. However, Z907 had a demerit of being low in photoelectron conversion efficiency due to the low absorption spectrum intensity in a visible to ultraviolet range in comparison to N3 and N719.

Although recently published ruthenium dyes include a ruthenium complex having a pyridylquinoline derivative as a ligand (Patent Document 1), a ruthenium complex having a terpyridine derivative as a ligand (Patent Documents 2 to 4), etc., none of these can improve both the photoelectric conversion efficiency and the durability.

Furthermore, very recently, Graetzel et. al. reported a photosensitizer dye with a specific structure having a 2,2'-bipyridine ligand (Patent Documents 5 and 6 and Non-Patent Document 3). However, because the absorption spectrum intensity in the visible-ultraviolet range still cannot be said to be adequate and the photoelectric conversion efficiency is low in a correlation to a redox potential, further improvement of the photoelectric conversion efficiency is desired.

Also, a wide range of photosensitizer dyes with a specific structure having a 2,2'-bipyridine ligand are reported in Patent Document 7. However, it is considered that further improvement is required in regard to stability of the actually cited dyes.

Development of a ruthenium complex or other transition metal complex as a new photosensitizer dye exhibiting strong absorption over a wider spectral range and being excellent in stability is thus desired.

Patent Document 1; Japanese Patent Laid-Open No. 2003-272721
Patent Document 2: Japanese Patent Laid-Open No. 2003-212851
Patent Document 3: Japanese Patent Laid-open No. 2005-47857
Patent Document 4: Japanese Patent Laid-Open No. 2005-120042
Patent Document 5: European Patent Application Publication No. 1622178
Patent Document 6: International Patent Publication No. WO 2006/010290
Patent Document 7: Japanese Patent Laid-Open No. 2001-271534
Non-Patent Document 1; J. Phys. Chem. B 2003, 107, 14336-144337
Non-Patent Document 2: Nature Material, p 402, Vol. 2, 2003
Non-Patent Document 3: J. Am. Chem. Soc. 2005, 127, 808-809

DISCLOSURE OF THE INVENTION

An object of the present invention is to provide a new transition metal complex, useful au a photosensitizer dye that improves both photoelectric conversion efficiency and durability, an oxide semiconductor electrode, having the transition metal complex adsorbed on an oxide semiconductor, and a dye-sensitized solar cell, using the oxide semiconductor electrode.

With the present invention, upon synthesizing a bivalent transition metal complex constituted of: (i) a bipyridyl polyacidic ligand, such as a dicarboxybipyridyl (dcbpy) ligand, as an adsorption site for adsorption onto titanium dioxide particle surfaces; (it) a ligand, selected from the group consisting of an isothiocyanato ion, an isocyanato group, and an isoselenocyanato group and enabling absorption and excitation at long wavelengths and charge transfer; and (iii) a bipyridyl (bpy) ligand, having an alkyl group, preferably a long-chain alkyl group, and a conjugately bonded thienylvinylene group, aminophenylenevinylene group, etc., the alkyl group imparting stability of a sensitizer dye against a nucleophile, the sensitizer dye improving an absorbance of a ruthenium complex or other transition metal complex and having stronger bathochromic effect in absorption; and using the bivalent transition metal complex as a photosensitizer dye of a dye-sensitized solar cell, success was achieved in providing a photoelectric conversion element with an excellent durability and a high photoelectric conversion characteristic.

That is, a bivalent transition metal complex according to a first aspect of the present invention is expressed by the following formula (I):

$$ML^1L^2A_2 \qquad (I)$$

where, in the formula (I), M is a bivalent iron ion, ruthenium ion, or osmium ion, each A is independently an isothiocyanato group (—NCS), an isocyanato group (—NCO), or an isoselenocyanato group (—NCSe).

L¹ in the formula (I) is expressed by the following formula (a1):

[Chemical Formula 1]

(a1)

where, in the formula (a1), each R¹ is independent with at least one being a carboxyl group, a phosphate group, a sulfonate group, or a salt of any of the above, and each remaining R¹, if any, being a hydrogen atom, and each R² is independent with at least one being a carboxyl group, a phosphate group, a sulfonate group, or a salt of any of the above, and each remaining R², if any, being a hydrogen atom, and L² in the formula (I) is expressed by the following formula (b1):

[Chemical Formula 2]

(b1)

where, in the formula (b1), each n independently denotes an integer no less than 0 and no more than 3, each Y independently denotes a hydrogen atom or Ar, and each Ar independently being expressed by either of the following structural formulae (c1) and (c2):

[Chemical Formula 3]

(c1)

where, in the formula (c1), X denotes a sulfur atom, oxygen atom, or nitrogen atom, each Z independently denotes a hydrogen atom or an alkyl group or alkoxy group having 1 to 16 carbons that may be substituted with a fluoro group, with at least one Z being an alkyl group or alkoxy group.

An oxidized semiconductor electrode according to a second aspect of the present invention has a photosensitizer dye, with a structure of the transition metal complex according to the first aspect, adsorbed on an oxide semiconductor.

A dye-sensitized solar cell according to a third aspect of the present invention is constituted of an anode, a charge transfer substance or an organic hole transfer substance, and a cathode, wherein the anode is comprised of the oxide semiconductor electrode according to the second aspect.

The new transition metal complex according to the present invention is an amphiphilic dye of excellent stability that is improved in terms of desorption phenomenon by introduction of a hydrophobic alkyl group, preferably a long-chain alkyl group. Also, a high molecular extinction coefficient in a visible-ultraviolet range is realized due to the introduction of the bipyridyl ligand, having a conjugately bonded thienylvinylene group, aminophenylenevinylene group, etc., a high photoelectric conversion characteristic is provided in the photosensitizer dye. Furthermore, in the dye-sensitized solar cell in a solid state, the dye acts as a spacer between titanium oxide and a hole conductor, and the long alkyl chain and the conjugate bond structure of the thiophenylvinylene group, aminophenylenevinylene group, etc., effectively enhances the spacer effect and blocks recombination of electrons. This also contributes to improved performance of the solid-state dye-sensitized solar cell.

BEST MODES FOR CARRYING OUT THE INVENTION (I) First Aspect of the Present Invention This aspect relates to a transition metal complex, which is expressed by the formula ML¹L²A₂ (I), described below, and is especially useful as a photosensitizer dye.

(i) Transition Metal Ion M

A transition metal ion M in the formula (I) is a bivalent Iron ion, ruthenium ion, or osmium ion, and from a standpoint of cell performance or environmental impact, the bivalent ruthenium ion or iron ion is preferable, and the bivalent ruthenium ion is especially preferable.

(ii) Ligand A

A ligand A in the formula (I) is an isothiocyanato group (—NCS), an isocyanato group (—NCO), or an isoselenocyanato group (—NCSe), and from a standpoint of electron donating property, the isothiocyanato group or the isoselenocyanato group is preferable, and the isothiocyanato group is especially preferable. It is especially preferable for the two ligands A to be both isothiocyanato groups.

(iii) Ligand L¹

A ligand L¹ in the formula (I) is expressed by the following formula (a1);

[Chemical Formula 4]

(a1)

In the formula (a1), each $R^1$ is independent with at least one being a carboxyl group, a phosphate group, a sulfonate group, or a salt of any of the above, and each remaining $R^1$, if any, being a hydrogen atom, and each $R^2$ is independent with at least one being a carboxyl group, a phosphate group, a sulfonate group, or a salt of any of the above, and each remaining $R^2$, if any, being a hydrogen atom.

As the substituents $R^1$ and $R^2$, from a standpoint of chemically bonding to titanium oxide or other oxide semiconductor and enabling efficient injection of electrons, the carboxyl group or the phosphate group is preferable, and the carboxyl group is especially preferable.

Also preferably, one each of the substituents $R^1$ and $R^2$ is a group selected from the group consisting of the carboxyl group, the phosphate group, the sulfonate group, or the salt of any of the above and more preferably, these are substituents of the same chemical species from the above mentioned standpoint of chemical bonding and electron injection. In this case, the remaining $R^1$'s and $R^2$'s are hydrogen atoms.

In terms of a π-conjugated electron chain, the positions of the $R^1$ and $R^2$ are preferably positions 4 and 4' as shown in the formula (a2) below:

[Chemical Formula 5]

(a2)

As salts of the substituents $R^1$ and $R^2$, salts formed with an alkali metal or quaternary ammonium can be cited as examples.

(iv) Ligand L²

A ligand L² in the formula (I) is expressed by the following formula (b1):

[Chemical Formula 6]

(b1)

In the formula (b1), each n independently denotes an integer of no less than 0 and no more than 3 and is preferably 0 from a standpoint of structural stability.

Each Y independently denotes a hydrogen atom or Ar, and preferably from a standpoint of structural symmetry, the two Y's are both the same chemical species, that is, are both Ar or both hydrogen atoms, and from a standpoint of electron conjugation property, hydrogen atoms are preferable.

Each Ar is independently expressed by either of the following structural formulae (c1) and (c2), and preferably from a standpoint of structural symmetry, the two Ar's are both the same chemical species, that is, are both (c1) or both (c2), and from a standpoint of cell performance based on experiments, the formula (c1) is more preferable.

(c1)

In the formula (c1), X denotes a sulfur atom, oxygen atom, or nitrogen atom, each Z independently denotes a hydrogen atom or an alkyl group or alkoxy group having 1 to 16 carbons that may be substituted with a fluoro group, with at least one Z being an alkyl group or alkoxy group. The factor that at least one of the Z's in (c1) is/are an alkyl group or an alkoxy group imparts the complex compound structure with hydrophobicity and steric structure, enabling a hydroxyl group or other nucleophile mixed in an electrolytic solution to be kept further away from the complex molecule and thereby significantly suppressing desorption of the complex molecule and improving stability of the complex molecule.

As the X in the formula (c1), from a standpoint of advantage of a π-electron conjugated system, an oxygen atom or a sulfur atom is preferable, and among these, a sulfur atom is especially preferable.

In regard to the Z's in the formula (c1), in terms of imparting hydrophobicity and an appropriate steric structure, at least one of the Z's is preferably an alkyl group or alkoxy group and especially preferably an alkyl group. When a Z is an alkyl group or an alkoxy group, the number of carbon atoms thereof is, from the standpoint of imparting hydrophobicity and an appropriate steric structure, 1 to 16, preferably 4 to 10, and more preferably 5 to 8 and, from the standpoint of an appropriate steric structure, the position thereof is preferably position 5 of a hetero five-membered ring as shown in the following formula (c11). In a case where the substituent Z is an alkyl group or an alkoxy group, it may be substituted with one or a plurality of fluoro groups from a standpoint of suitability with respect to a solid electrolyte.

(c11)

(c11)

The formulae (b2) or (b21), indicated below, can be cited as especially preferable forms of the ligand $L^2$, and from a standpoint of cell characteristics, (b2) and especially (b21) are more preferable.

[Chemical Formula 9]

(b2)

In the formula (b2), each X independently denotes a sulfur atom, oxygen atom, or nitrogen atom, is preferably an oxygen atom or a sulfur atom, and especially preferably a sulfur atom. Each of $R^4$ and $R^5$ independently denotes a hydrogen atom or an alkyl group or alkoxy group having 1 to 16 carbons that may be substituted with a fluoro group, with at least one of the $R^4$'s and at least one of the $R^5$'s being an alkyl group or alkoxy group, especially preferably an alkyl group, with 1 to 16 carbons, more preferably 4 to 10 carbons, and even more preferably 5 to 8 carbons, and especially preferably, one of $R^4$'s and one of $R^5$'s is an alkyl group or alkoxy group, especially preferably an alkyl group, with 1 to 16 carbons, more preferably 4 to 10 carbons, and even more preferably 5 to 8 carbons.

[Chemical Formula 10]

(b21)

In the formula (b21), each X independently denotes a sulfur atom, oxygen atom, or nitrogen atom, is preferably an oxygen atom or a sulfur atom, and especially preferably a sulfur atom. Each of $R^4$ and $R^5$ independently denotes an alkyl group or alkoxy group, especially preferably an alkyl group, that may be substituted with a fluoro group and has 1 to 16 carbons, more preferably 4 to 10 carbons, and even more preferably 5 to 8 carbons; and furthermore preferably, each of $R^4$ and $R^5$ independently is an alkyl group or alkoxy group, especially preferably an alkyl group, having 1 to 16 carbons, more preferably 4 to 10 carbons, and even more preferably 5 to 8 carbons.

[Chemical Formula 11]

(b3)

(v) A structure of the transition metal complex according to the present aspect that is especially preferable as a photosensitizer dye is denoted by the following formula (II), and from a standpoint of cell characteristics, the formula (II) is preferable.

[Chemical Formula 12]

[Chemical Formula 12]

(II)

In the formula (II), X, $R^4$, and $R^5$ have the same meanings as the X, $R^4$, and $R^5$ in the formula (b21), and each of $R^1$ and $R^2$ independently denotes a carboxyl group, a phosphate group, a sulfonate group, or a salt of any of the above.

(vi) Although in regard to a method for synthesizing the transition metal complex according to the present aspect, any known method may be employed, for example, when ruthenium is employed as the transition metal, production may be carried out by making the bipyridyl ligands (a1) and (b1) act sequentially on a dihalogeno(p-cymene)ruthenium (II) dimer, preferably dichloro(p-cymene)ruthenium (II) dimer, and thereafter using a salt containing the ligand A, for example, when the isothiocyanato group is to be used as the ligand A, ammonium isothiocyanate or other isothiocyanate salt to replace a halogen on the ruthenium with the isothiocyanato group.

A commercially sold product may be used in regard to the ligand $L^1$.

The ligand $L^2$ may be obtained by synthesizing by any method. For example, the $L^2$ having the structure of the formula (b2) can be produced, for example, by making a base (n-butyllithium, etc.) and a formaldehyde source, such as dimethylformamide, act on an alkylthiophene to produce an alkylthiophene-2-carbaldehyde, making the alkylthiophene-2-carbaldehyde undergo an addition reaction with a product obtained by making LDA or other base act on 4,4'-dimethyl-2,2'-bipyridine, and then using pyridinium p-toluenesulfonate or other acid catalyst to dehydrate the addition product obtained.

(II) Second Aspect of the Present Invention

This aspect provides an oxide semiconductor electrode, having a photosensitizer dye, with the structure of the transition metal complex according to the first aspect, adsorbed on an oxide semiconductor.

As a method for making the transition metal complex become adsorbed on an oxide semiconductor thin film, any known method may be employed, and methods where an oxide semiconductor thin film of titanium dioxide, etc., is immersed in a solution of the transition metal complex dye at a predetermined temperature (dipping method, roller method, air knife method, etc.) and methods where a ruthenium dye solution is applied onto a surface of an oxide semiconductor layer (wire bar method, application method, spinning method, spraying method, offset printing method, screen printing method, etc.) can be cited as examples.

(IV) Third Aspect of the Present Invention

This aspect provides a dye-sensitized solar cell constituted of an anode, a charge transfer substance or an organic hole transfer substance, and a cathode, wherein the anode is comprised of the oxide semiconductor electrode according to the second aspect.

As a charge transfer substance or an organic hole transfer substance, a liquid electrolyte, containing a redox electrolyte, can be cited as an example, and as a redox electrolyte, an $I^-/I^{3-}$ System, $Br^{2-}/Br^{3-}$ system, quinone/hydroquinone system, etc., can be cited as examples.

A more detailed description shall now be provided by citing specific examples of the present invention.

Synthesis Example 1

Synthesis of 4,4'-bis[2-(5-hexyl-2-thienyl)vinyl]-2,2'-bipyridine (1) Synthesis of 5-hexylthiophene-2-carbaldehyde

[Chemical Formula 14]

Under a nitrogen atmosphere at 0° C., 24 ml of n-butyllithium (1.6M in hexane) were added by dripping to a THF solution containing 2-hexylthiophene (5 g). The solution was then stirred for another 15 minutes and, after adding DMF (5 ml), set to room temperature. The resulting solution was then poured into a IN ammonium chloride solution and extracted with methylene chloride. An organic layer was washed with water and dried with anhydrous magnesium sulfate. A crude product was collected by removing the solvent and then purified by a column chromatograph (carrier: silicon dioxide; eluate: hexane/methylene chloride-4/1 (volume ratio)) to obtain 4.6 g of a product.

(2) Synthesis of 4,4'-bis[2-hydroxy-2-(5-hexyl-2-thienyl)ethyl]-2,2'-bipyridine

[Chemical Formula 15]

Under a nitrogen atmosphere at 0° C., 16 ml (0.0256 mol) of n-butyllithium (1.6M in hexane) were added to a dry tetrahydrofuran (60 ml) solution of diisopropylamine (3-1 ml, 0.0123 mol). The light yellow solution was then stirred for 20 minutes at 0° C. A dry tetrahydrofuran (50 ml) solution of 4,4'-dimethyl-2,2'-bipyridine (1.74 g, 0.0135 mol) was then added by dripping. The reaction solution, which became dark orange-red in color, was stirred at 0° C. for 75 minutes, and then a dry tetrahydrofuran (25 ml) solution of 5-hexylthiophene-2-carbaldehyde (3.72 g, 0.027 mol) was added over a period of 5 minutes. This was stirred at 0° C. for 75 minutes and then stirred further at room temperature for 5 hours. Thereafter, 3 ml of methanol was added to the solution to stop the reaction. 50 mol of water were then added, and a product was extracted three times with 50 ml of methylene chloride. 50 ml of an organic layer was washed with 50 ml of saline water and dried with anhydrous magnesium sulfate. After distillation, 3.0 g of a white-colored product was obtained.

(3) Synthesis of 4,4'-bis[2-(5-hexyl-2-thienyl)vinyl]-2,2'-bipyridine

[Chemical Formula 16]

4,4'-bis[2-hydroxy-2-(5-hexyl-2-thienyl)ethyl]-2,2'-bipyridine (1.5 g) was dissolved in 110 g of toluene containing pyridindium p-toluenesulfonate (0.2 g) and reflux was performed for 4 hours using a Dean-Starc device. The solvent was distilled off under reduced pressure, and a residue was dissolved in methylene chloride and washed with a saturated solution of sodium bicarbonate. An organic layer was washed with anhydrous magnesium sulfate and distilled to obtain 1.2 g of a yellow-colored product.

Synthesis Example 2

Synthesis of Ru($L^3$) ($L^4$)(NCS)$_2$ (J2)

$L^3$=2,2'-bipyridine-4,4'-dicarboxylic acid
$L^4$=4,4'-bis[2-(5-hexyl-2-thienyl)vinyl]-2,2'-bipyridine

[Chemical Formula 17]

Figure 6:
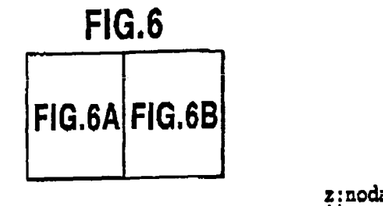
FIG. 6A shows a high magnetic field side of a ¹H-NMR spectrum of the ruthenium dye J2 according to the present invention and FIG. 6B shows a low magnetic field side of the ¹H-NMR spectrum of the ruthenium dye J2 according to the present invention.
Figure 6A:
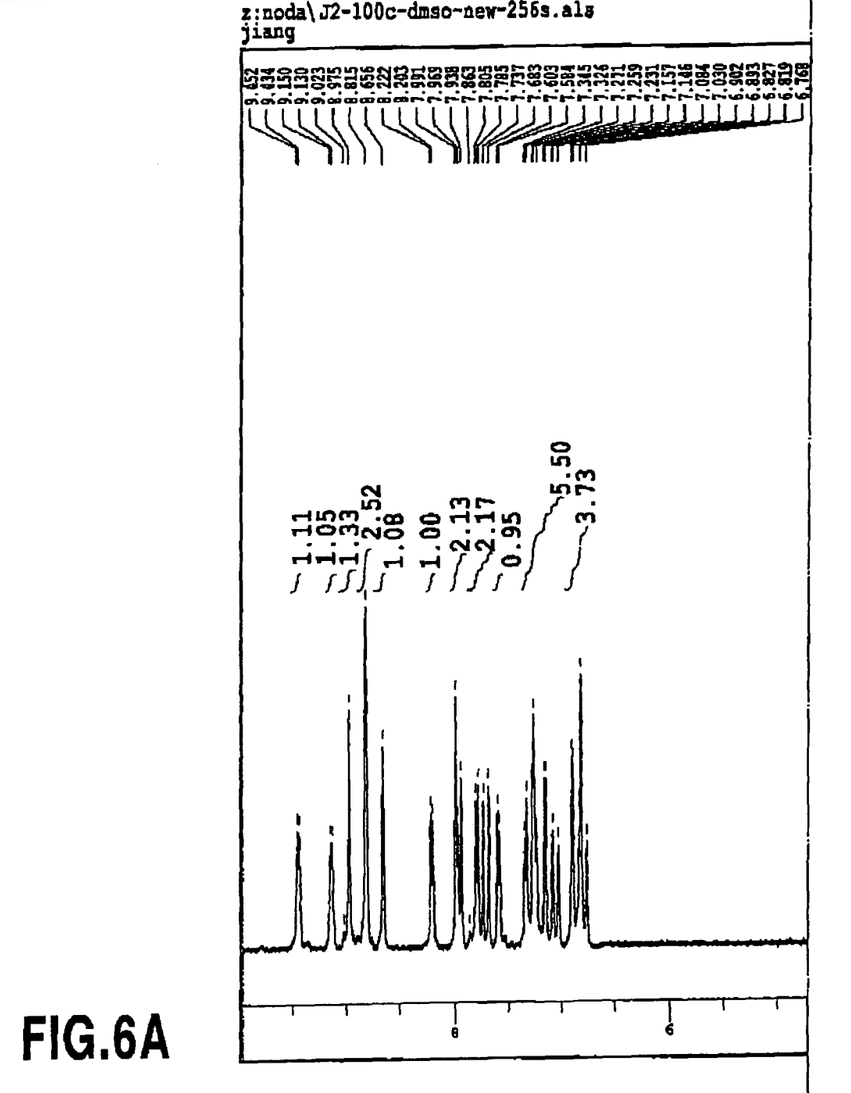
Figure 6B:
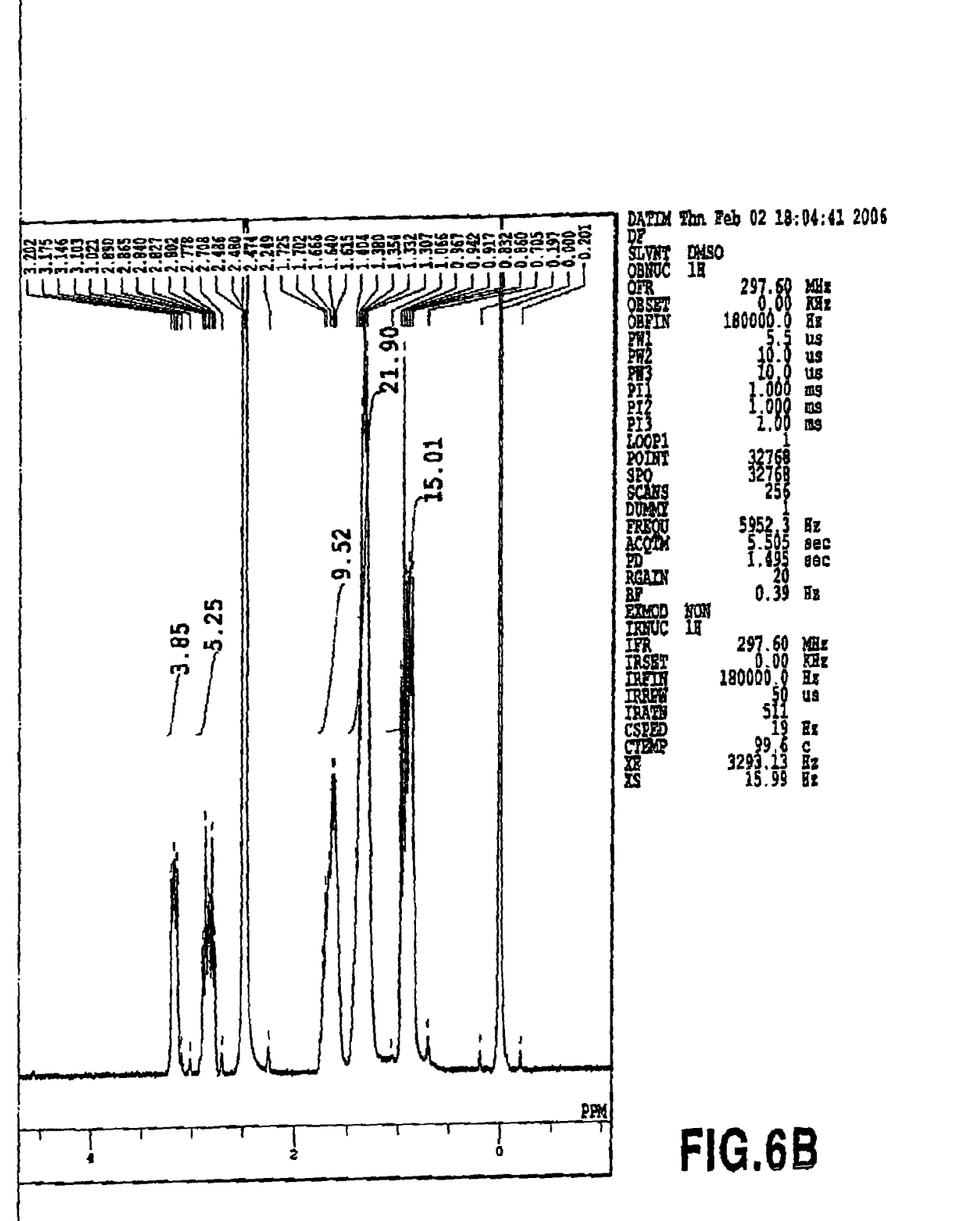

A 10 ml DMF solution of 4,4'-bis[2-(5-hexyl-2-thienyl)vinyl]-2,2'-bipyridine (0.15 g, 0.245 mmol) and dichloro(p-cymene)ruthenium (II) dimer (0.0747 g, 0.122 mmol) was heated by microwave (200 W) under a dark, nitrogen atmosphere at 60° C. for 10 minutes. 2,2'-bipyridine-4,4'-dicarboxylic acid (0.12 g, 0.49 mmol) was then added and heating at 150° C. was performed for 10 minutes. The temperature was then cooled to 100° C., and then ammonium thiocyanate (solution of 0.5 g in 4 ml of water) was added and made to react for 10 minutes at 120° C. The temperature was then lowered to room temperature and DMF was distilled under vacuum. 80 ml of water was added to the residue and the residue was thus immersed for 30 minutes. Insolubles were collected and washed with water and diethyl ether. A crude product was dissolved along with TBAOH (tetrabutylammonium hydroxide) in methanol, and using methanol as an eluate, purification was performed with a Sephadox LH-20 column. A product of a main layer was recovered and condensed, and 0.2M nitric acid was added to obtain a precipitate. The product was collected and after drying in vacuum at room temperature, 0.31 g of a ruthenium complex (J2) was obtained. A $^1$H-NMR (300 MHz) spectrum of J2 is shown in FIGS. 6A and 6B.

Figure 4:
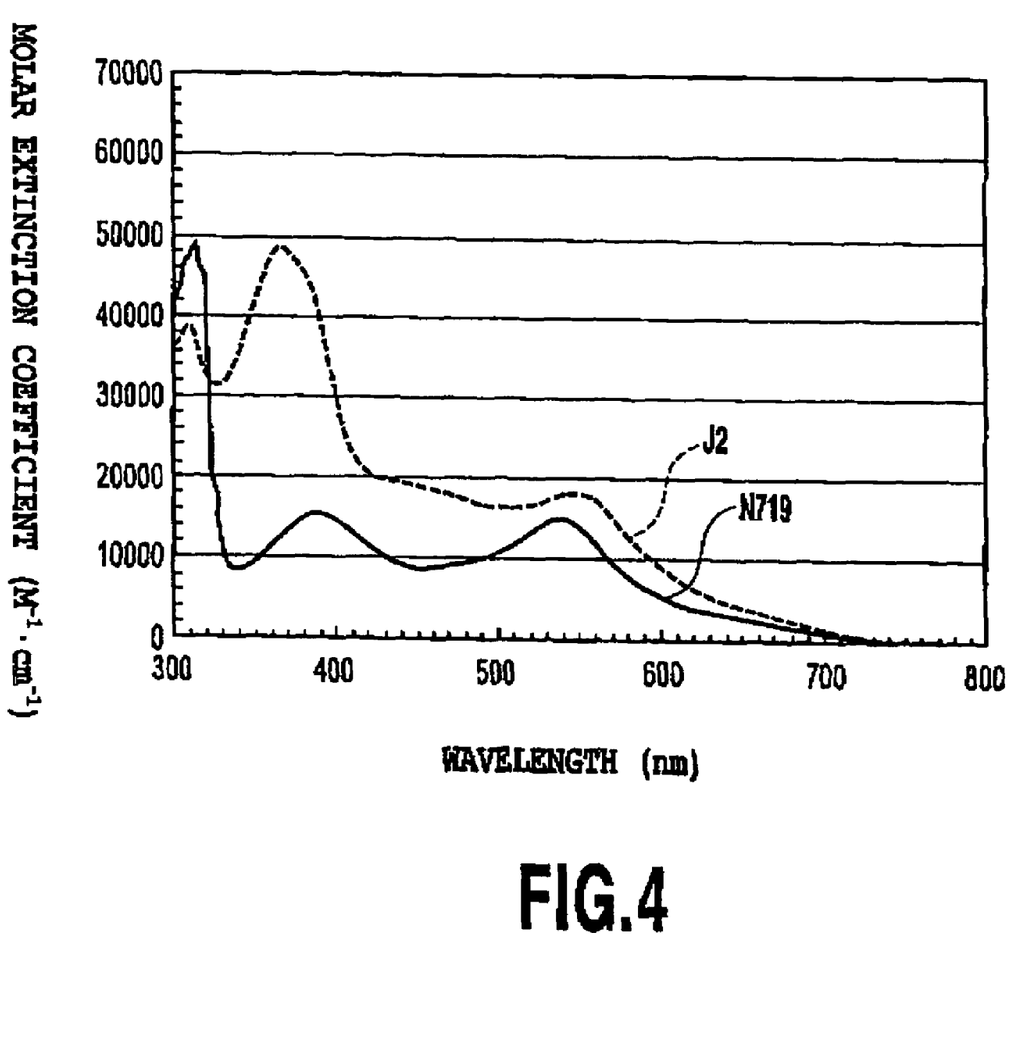
FIG. 4 shows an absorption spectrum of N719 (comparative product) and the absorption spectrum of the ruthenium dye J2 according to the present invention.

$^1$H-NMR ($\delta_H$/ppm in DMSO) in the aromatic regions: 9.44 (d, 1H), 9.16 (d, 1H), 8.97 (s, 1H), 8.83 (s, 1H), 8.79 (s, 1H), 8.69 (s, 1H), 8.24 (d, 1H), 8.00 (d, 1H), 7.97 (d, 1H), 7.87 (d, 1H), 7.78 (d, 1H), 7.72 (d, 1H), 7.58 (d, 1H), 7.36 (d, 1H), 7.27 (d, 1H), 7.14 (d, 1H), 7.09 (d, 1H), 6.90 (d, 1H), 6.82 (d, 2H), 6.80 (d, 1H). MS-ESI m/z: 1001.5 (M-H)$^+$ Examples Performance Evaluation (1) Absorption Spectrum (FIGS. 1 and 4)

Figure 1:
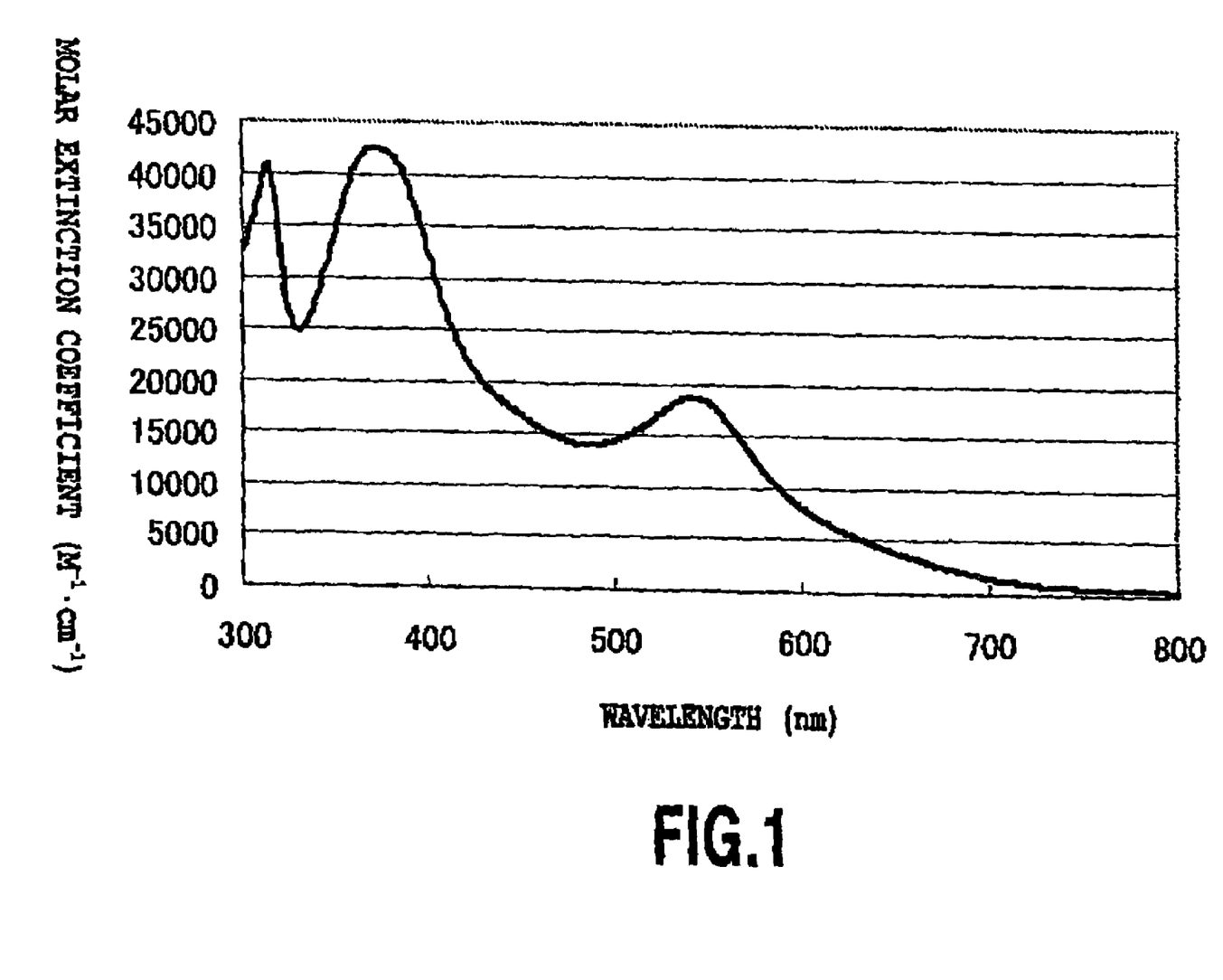
FIG. 1 shows an absorption spectrum of a ruthenium dye J2 according to the present inventions.

FIG. 1 shows an absorption spectrum of J2, which is a product according to the present invention. FIG. 4 shows an absorption spectrum of N719, which is a comparative product, measured in the same manner.

Figure 2:
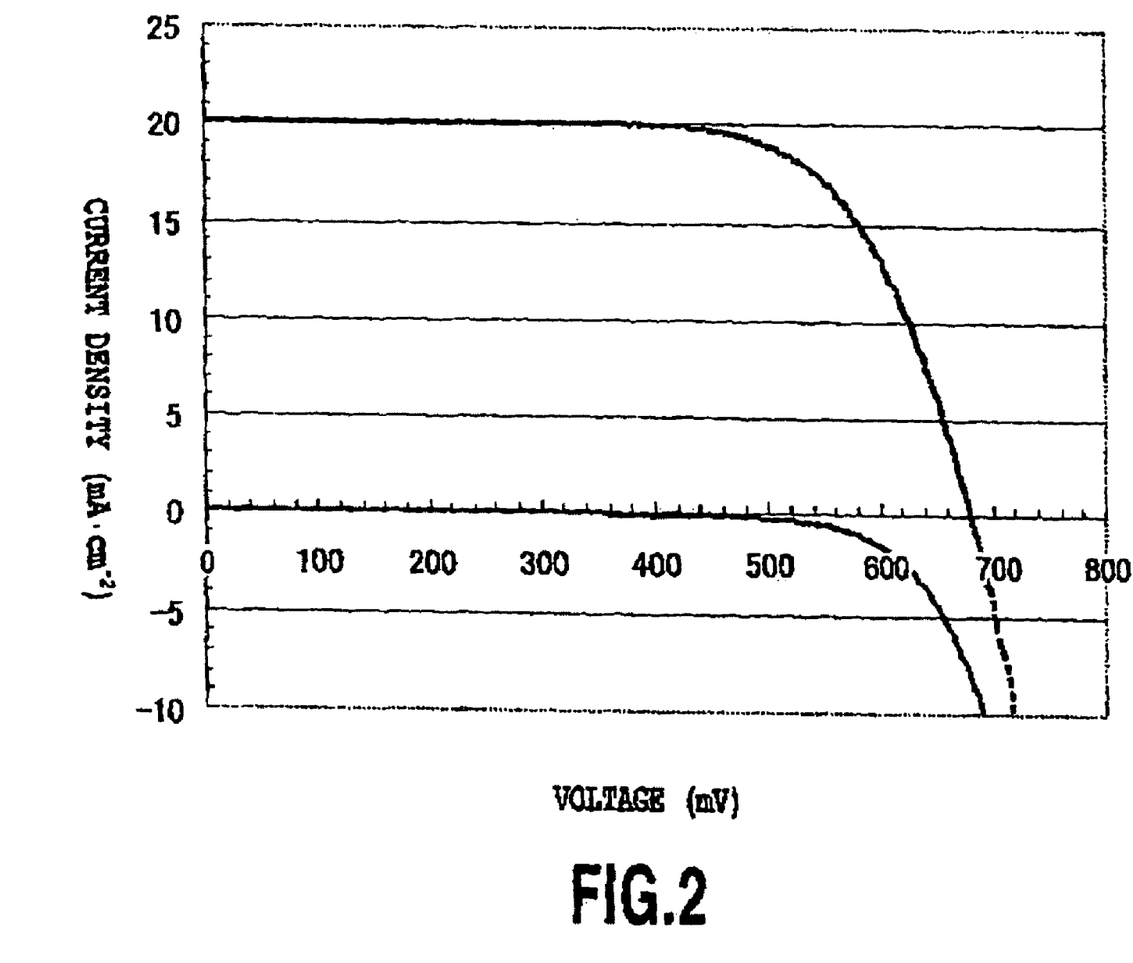
FIG. 2 shows a current-voltage curve of a dye-sensitized solar cell using the ruthenium dye J2 according to the present invention.
Figure 3:
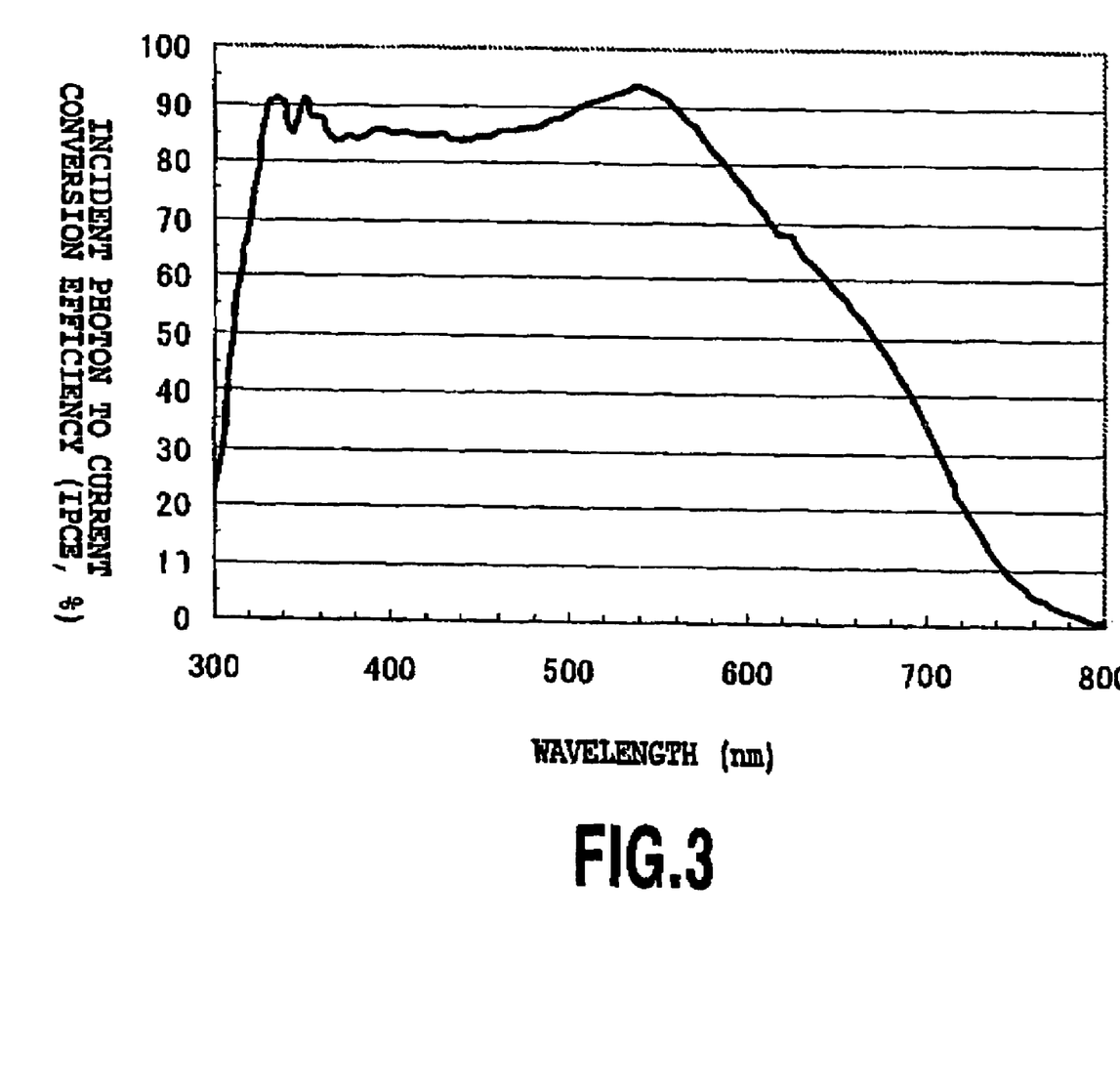
FIG. 3 shows an incident photon to current conversion efficiency (IPCE) of the ruthenium dye J2 according to the present invention.

(2) Cell Performance Evaluation 1 (FIGS. 2 and 3)

Titanium dioxide (average particle diameter: 20 nm), prepared by a method in Non-Patent Document 1, was coated to a film thickness of 13 μm onto FTO dielectric glass by a doctor blade method and heating at 450° C. was performed for 30 minutes. A scattering layer (material: titanium dioxide with an average particle diameter of 400 nM) of 4 μm then applied and heating at 500° C. was performed for 20 minutes. The thin film was then treated with 0.05M titanium tetrachloride and then heated at 450° C. for 30 minutes. Titanium dioxide thin films thus obtained were then immersed at 65° C. for 2 hours in the following ruthenium dye solutions, respectively.

J2: 0.3 mM solution of J2 [solvent: 1:1 (volume ratio) mixed solvent of acetonitrile and t-butyl alcohol containing 1.47 mM chenodeoxycholic acid]

N3: 0.3 mM solution of N3 [solvent: 1:1 (volume ratio) mixed solvent of acetonitrile and t-butyl alcohol]

N719: 0.3 mM solution of N719 [solvent: 1:1 (volume ratio) mixed solvent of acetonitrile and t-butyl alcohol]

Z907: 0.3 mM solution of Z907 [solvent: 1:1 (volume ratio) mixed solvent of acetonitrile and t-butyl alcohol]

Each anode thus prepared was overlapped with a platinum-coated ITO counter electrode, and an intermediate layer was filled with an electrolytic solution constituted of 0.05M iodine ($I_2$), 0.1M lithium iodide, 0.6M 1-propyl-3-methylimidazoliumiodide, 0.5 Mt-butylpyridine and a 1:1 (volume ratio) mixed solvent of acetonitrile and valeronitrile.

Results of measuring cell characteristics of dye-sensitized solar cells thus prepared are shown in Table 1.

That is, using a solar simulator (made by Yamashita Denso Corp.), simulated solar light with an AM (air mass) of 1.5 and 100 mW/cm$^2$ was illuminated, a short-circuit current density, an open-circuit voltage, and a fill factor (FF) were measured, and a photoelectric conversion efficiency was computed based on the following calculation equation (Equation 1):

Photoelectric conversion efficiency(%)=100×(short-circuit current density×open-circuit voltage×fill factor)/(illuminated solar light energy)　　(Equation 1)

TABLE 1

| Name of dye | Jsc (mA/cm$^2$)[1] | Voc (V)[2] | FF[3] | η (%)[4] |
|---|---|---|---|---|
| J2 (invented product) | 20.00 | 0.68 | 0.70 | 9.52 |
| N3 | 16.4 | 0.66 | 0.67 | 7.29 |
| N719 | 18.47 | 0.64 | 0.72 | 8.46 |
| Z907 | 15.5 | 0.69 | 0.65 | 6.93 |

[1]current density
[2]open-circuit voltage
[3]fill factor
[4]photoelectric conversion efficiency Voltage vs. current density characteristics of the dye-sensitized solar cell prepared using the J2 dye is shown in FIG. 2, and an incident photon to current conversion efficiency of the dye-sensitized solar cell prepared using the J2 dye is shown in FIG. 3.

The structural formulae of N-3, N719, and Z907 are shown below.

[Chemical Formula 20]

(N3)

[Chemical Formula 21]

(N719)

[Chemical Formula 22]

(Z907)

(3) Cell Performance Evaluation 2

After coating a commercially sold titanium oxide paste (trade name; PST-18NR; manufacturer: Catalysts & Chemicals Industries Co., Ltd.; average particle diameter: 20 μm) onto PTO conductive glass to a film thickness of 14 μm and drying at 130° C., a scattering layer paste (trade name: PST-400C; manufacturer; Catalysts & Chemicals Industries Co., Ltd.; average particle diameter, 400 μm) was applied on, and heating by raising the temperature in stepwise manner to 500° C. was performed. Titanium dioxide thin films thus obtained were then immersed at 68° C. for 3 hours in the following ruthenium dye solutions, respectively. J2: 0.18 mM solution of J2 [solvent: 1:1 (volume ratio) mixed solvent of acetonitrile and t-butyl alcohol containing 0.90 mM chenodeoxycholic acid]

K19-4[*1]: 0.25 mM solution of K19-4 [solvent: 1:1 (volume ratio) mixed solvent of acetonitrile and t-butyl alcohol containing 0.40 mM chenodeoxycholic acid]

Each anode thus prepared was overlapped with a platinum-coated ITO counter electrode and an intermediate layer was filled with an electrolytic solution constituted of 0.05M iodine ($I_2$), 0.1M lithium iodide, 0.6M 1-propyl-3-methylimidazoliumiodide, 0.5M t-butylpyridine, and a 1:1 (volume ratio) mixed solvent of acetonitrile and valeronitrile.

Results of measuring cell characteristics of dye-sensitized solar cells thus prepared are shown in Table 2.

TABLE 2

| Name of dye | Jsc (mA/cm$^2$)[*2] | Voc (V)[*3] | FF[*4] | η (%)[*5] |
|---|---|---|---|---|
| J2 | 18.20 | 0.686 | 0.684 | 8.55 |
| K19-4 | 15.19 | 0.661 | 0.672 | 6.75 |

Figure 5:
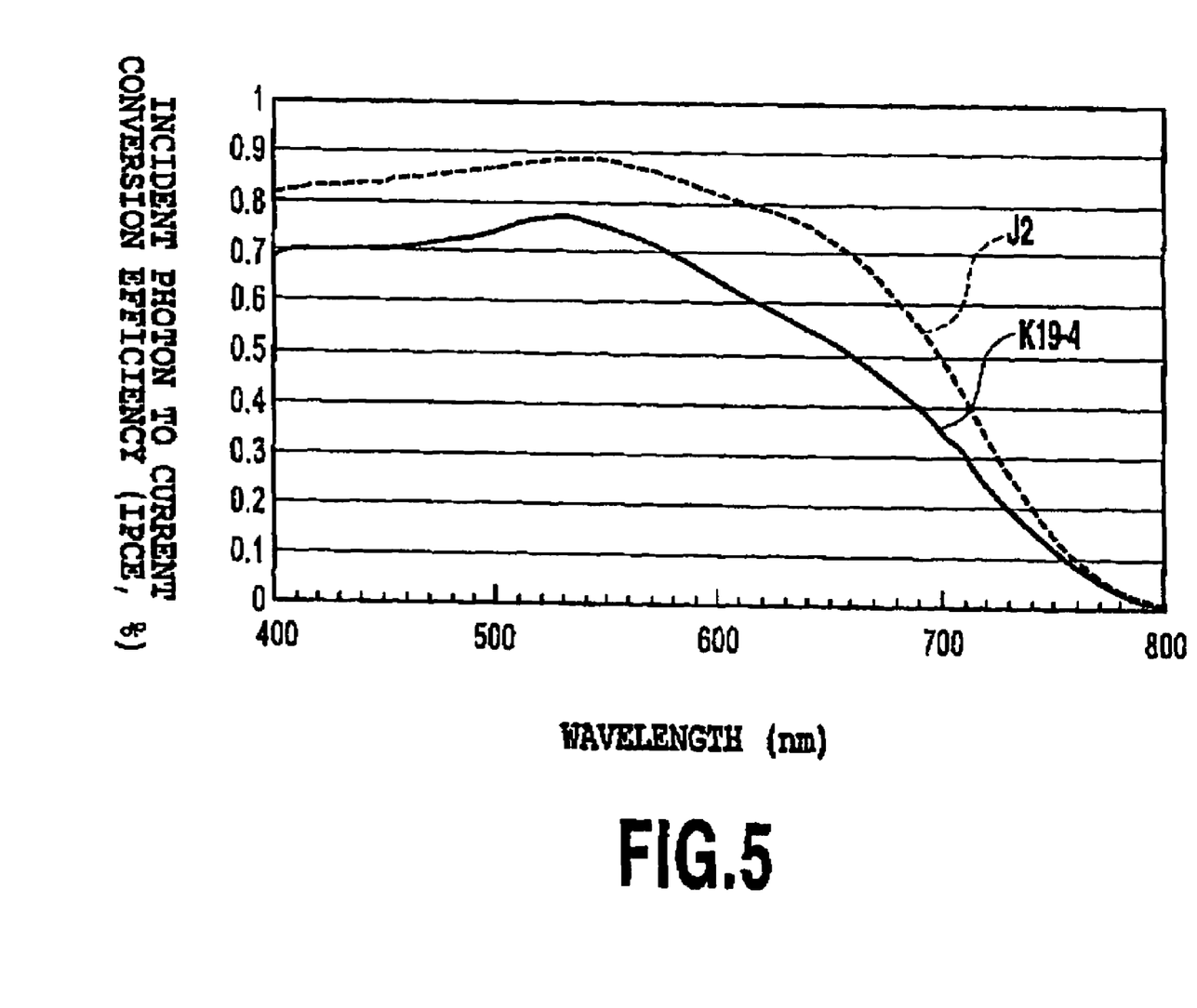
FIG. 5 shows an incident photon to current conversion efficiency (IPCE) of K19-4 (comparative product) and the incident photon to current conversion efficiency (IPCE) of the ruthenium dye J2 according to the present invention.

[*2]current density
[*3]open-circuit voltage
[*4]fill factor
[*5]photoelectric conversion efficiency Incident photon to current conversion efficiencies of the dye-sensitized solar cells prepared as described above are shown in FIG. 5.

As shown in Table 2, even in comparison to K19, J2 exhibits a clear superiority in cell characteristics. The IPCE curves shown in FIG. 5 also support this superiority.

*1: K19-4, having the structural formula shown below, was synthesized by using n-butyl iodide in place of hexyl iodide in 1) of Example I of Patent Document 6 and otherwise carrying out procedures in the same manner as in 1) and 4) to 7) of Example I and in Example III.

[Chemical Formula 23]

(4) Durability

A durability of Z907 in reported in Non-Patent Document and according to this, Z907 maintained no less than 94% of its initial performance after 1000 hours under a heated condition of 80° C. From its structure, the J2 dye, which is a product of the present invention, has an equivalent performance.

INDUSTRIAL APPLICABILITY

Because the transition metal complex dye according to the present invention has a high molecular extinction coefficient in the visible-ultraviolet range and has excellent durability, it is useful as a photoelectric conversion element of a dye-sensitized solar cell, etc.

The invention claimed is:

1. A bivalent transition metal complex expressed by the formula (I):

where, in the formula (I), M is a bivalent iron ion, ruthenium ion, or osmium ion, each A is independently an isothiocyanato group (—NCS), an isocyanato group (—NCO), or an isoselenocyanato group (—NCSe), $L^1$ in the formula (I) is expressed by the formula (a1):

where, in the formula (a1), each $R^1$ is independent with at least one being a carboxyl group, a phosphate group, a sulfonate group, or a salt of any of the above, and each remaining $R^1$, if any, being a hydrogen atom, and each $R^2$ is independent with at least one being a carboxyl group, a phosphate group, a sulfonate group, or a salt of any of the above, and each remaining $R^2$, if any, being a hydrogen atom, and $L^2$ in the formula (I) is expressed by the formula (b1):

where, in the formula (b1), each n independently denotes an integer of no less than 0 and no more than 3, each Y independently denotes a hydrogen atom or Ar, with each Ar independently being expressed as structural formulae (c1):

Ar—:

(c1)

where, in the formula (c1), X denotes a sulfur atom, oxygen atom, or nitrogen atom, each Z independently denotes a hydrogen atom or an alkyl group or alkoxy group having 1 to 16 carbons that may be substituted with a fluoro group, with at least one Z being an alkyl group or alkoxy group.

2. The transition metal complex according to claim 1, wherein all of the ligands A are isothiocyanato groups and M is a bivalent ruthenium ion.

3. The transition metal complex according to claim 1, wherein the $L^2$ is expressed by the formula (b2):

(b2)

where, in the formula (b2), each X independently denotes a sulfur atom, oxygen atom, or nitrogen atom, each $R^4$ independently denotes a hydrogen atom or an alkyl group or alkoxy group having 1 to 16 carbons that may be substituted with one or a plurality of fluoro groups, with at least one of the $R^4$'s being an alkyl group or alkoxy group, and each $R^5$ independently denotes a hydrogen atom or an alkyl group or alkoxy group having 1 to 16 carbons that may be substituted with one or a plurality of fluoro groups, with at least one of the $R^5$'s being an alkyl group or alkoxy group.

4. The transition metal complex according to claim 3, wherein each X independently denotes an oxygen atom or a sulfur atom, each $R^4$ independently denotes a hydrogen atom or an alkyl group having 1 to 16 carbons that may be substituted with one or a plurality of fluoro groups, with at least one of the $R^4$'s being an alkyl group, and each $R^5$ independently denotes a hydrogen atom or an alkyl group having 1 to 16 carbons that may be substituted with one or a plurality of fluoro groups, with at least one of $R^5$ being an alkyl group.

5. The transition metal complex according to claim 4, wherein the $L^1$ is expressed by the formula (a2):

(a2)

where, in the formula (a2), each of $R^1$ and $R^2$ independently denote a carboxyl group, a phosphate group, a sulfonate group, or a salt of any of the above.

6. A photosensitizer dye having a structure of the transition metal complex according to claim 1.

7. A dye-sensitized solar cell comprising: an anode, a charge transfer substance or an organic hole transfer substance, and a cathode, wherein the anode is comprised of an oxidized semiconductor electrode having the photosensitizer dye according to claim 6 absorbed on an oxide semiconductor.

* * * * *